United States Patent
Godschalx et al.

(10) Patent No.: US 7,381,850 B2
(45) Date of Patent: Jun. 3, 2008

(54) MULTIFUNCTIONAL UNSYMMETRICALLY SUBSTITUTED MONOMERS AND POLYARYLENE COMPOSITIONS THEREFROM

(75) Inventors: James P. Godschalx, Midland, MI (US); Robert E. Hefner, Jr., Lake Jackson, TX (US); Q. Jason Niu, Excelsior, MN (US); H. Craig Silvis, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/549,382

(22) PCT Filed: Apr. 1, 2004

(86) PCT No.: PCT/US2004/009973

§ 371 (c)(1),
(2), (4) Date: Jul. 17, 2006

(87) PCT Pub. No.: WO2004/089862

PCT Pub. Date: Oct. 21, 2004

(65) Prior Publication Data

US 2006/0267000 A1    Nov. 30, 2006

(51) Int. Cl.
*C07C 49/537* (2006.01)
*C08F 36/00* (2006.01)
*H01L 29/08* (2006.01)

(52) U.S. Cl. ............... 568/330; 526/283; 526/285; 257/40

(58) Field of Classification Search ............ None
See application file for complete search history.

(56) References Cited

U.S. PATENT DOCUMENTS

| 5,965,679 | A | 10/1999 | Godschalx et al. |
| 6,156,812 | A | 12/2000 | Lau et al. |
| 6,172,128 | B1 | 1/2001 | Lau et al. |
| 6,359,091 | B1 | 3/2002 | Godschalx et al. |

FOREIGN PATENT DOCUMENTS

| WO | WO00/31183 | 6/2000 |
| WO | WO03/068825 | 8/2003 |

OTHER PUBLICATIONS

J. Org. Chem. vol. 62, No. 11, 1997, pp. 3430-3431, Compounds 8a, 8c, 8d, 8d' In the left-hand column on p. 3431 and surrounding text.
J. Org. Chem. vol. 62, 1997, pp. 3432-3433, Compounds 7a, 7b.

*Primary Examiner*—Sikarl A. Witherspoon (57) ABSTRACT

A monomer suitable for use in forming low dielectric constant films in semiconductor devices comprising i) two dienophile groups (A-functional groups) attached to a single aromatic ring and ii) a second ring structure comprising two conjugated carbon-to-carbon double bonds and a leaving group L (B-functional group), characterized in that said single aromatic ring is directly covalently attached to one of the double bonded carbons of the B functional group or to a fused aromatic ring containing two such double bonded carbons of the B-functional group, and one A-functional group of one monomer is capable of reaction under cycloaddition reaction conditions with the B-functional group of a second monomer to thereby form a polymer.

11 Claims, 1 Drawing Sheet

Fig. 1

— Ex. 4, 12 H
--- Ex. 4, 24 H
—·— Ex. 4, 48 H
—··— Comparative, 48 H

Fig. 2

MULTIFUNCTIONAL UNSYMMETRICALLY SUBSTITUTED MONOMERS AND POLYARYLENE COMPOSITIONS THEREFROM

This invention was made with United States Government support under Cooperative Agreement No. 70NANB8H4013 awarded by NIST. The United States Government has certain rights in the invention.

FIELD OF THE INVENTION

This invention relates to compositions having at least two different reactive functional groups and to aromatic polymers made from these monomers. The resulting polymers are useful in making low dielectric constant insulating layers in microelectronic devices.

BACKGROUND OF THE INVENTION

Polyarylene resins, such as those disclosed in U.S. Pat. No. 5,965,679 (Godschalx et al.) are low dielectric constant materials suitable for use as insulating films in semiconductor devices, especially integrated circuits. Such polyarylene compounds are prepared by reacting polyfunctional compounds having two or more cyclopentadienone groups with polyfunctional compounds having two or more aromatic acetylene groups, at least some of the polyfunctional compounds having three or more reactive groups. Certain single component reactive monomers which contained one cyclopentadienone group together with two aromatic acetylene groups, specifically 3,4-bis(3-(phenylethynyl)phenyl)-2,5-dicyclopentadienone and 3,4-bis(4-(phenylethynyl)phenyl)-2,5-dicyclopentadienone, and polymers made from such monomers were also disclosed in the foregoing reference. Typically, these materials are B-staged in solvent solution and then spin coated onto a substrate followed by a hotplate baking step and a subsequent curing (vitrification) to 400-450° C. in an oven to complete the cure.

In U.S. Pat. No. 6,359,091, it was taught that it may be desirable to adjust the modulus of polymers as taught in Godschalx et al., by adjusting the ratio of the reactants in Godschalx or by adding other reactive species to the monomers or to the partially polymerized product of Godschalx. U.S. Pat. No. 6,172,128 teaches aromatic polymers containing cyclopentadienone groups that may react with aromatic polymers containing phenylacetylene groups to provide branched or cross-linked polymers. U.S. Pat. No. 6,156,812 shows polymers which contain both cyclopentadienone groups and phenyl acetylene groups in the backbone of the polymer. In WO00/31183, cross-linkable compositions comprising a cross-linkable hydrocarbon-containing matrix precursor and a pore forming substance (poragen) which are curable to form low dielectric constant insulating layers for semiconductor devices were disclosed. Generally, the foregoing disclosure taught the formation of improved (lower) dielectric constant insulating films by partially curing the precursor to form a matrix containing occlusions of the poragen and then removing the pore generating material to form voids or pores in the matrix material.

Although the foregoing advances have led to improvements in dielectric constant of the resulting film, additional improvements in film properties are desired by the industry. In particular, curable compositions capable of providing enhanced processability, improved solubility, and better substrate wet out are still desired. In addition, compositions having improved physical properties, especially as measured by the flexural storage modulus of the partially cured matrix, are also sought.

SUMMARY OF THE INVENTION

According to a first embodiment of the present invention there is provided a monomer comprising i) two dienophile groups (A-functional groups) attached to a single aromatic ring and ii) a second ring structure comprising two conjugated carbon-to-carbon double bonds and a leaving group L (B-functional group), characterized in that said single aromatic ring is directly covalently attached to one of the double bonded carbons of the B-functional group or to a fused aromatic ring containing two such double bonded carbons of the B-functional group, and one A-functional group of one monomer is capable of reaction under cycloaddition reaction conditions with the B-functional group of a second monomer to thereby form a polymer.

According to a second embodiment of this invention, there is provided a curable oligomer or polymer made by the reaction of the foregoing monomer, a mixture thereof, or a composition comprising the same under cycloaddition reaction conditions. In this embodiment of the invention the curable oligomer or polymer comprises some remainder of the two reactive functional groups as pendant groups, terminal groups, or as groups within the backbone of the oligomer or polymer.

According to a third embodiment this invention is a highly crosslinked polymer made by final cure of the foregoing curable oligomers or polymers or compositions comprising the same.

According to a fourth embodiment, this invention is a composition comprising the curable oligomer or polymer of the second embodiment and a poragen..

According to a fifth embodiment of the invention there is provided a method of forming a solid article comprising a vitrified polyarylene polymer which method comprises providing the above monomer, mixture of monomers, or a composition comprising the same; partially polymerizing the monomer under cycloaddition reaction conditions, optionally in the presence of a solvent and/or a poragen thereby forming a curable oligomer or polymer containing composition; and curing the composition to form a solid polyarylene polymer, optionally accompanied or followed by removal of the solvent and/or poragen.

According to a sixth embodiment, this invention is an article made by the above method or a construct containing such article.

According to a seventh embodiment of the invention, the foregoing article is a film and the construct is a semiconductor device, such as an integrated circuit, incorporating the film as an insulator between circuit lines or layers of circuit lines therein.

The monomers are highly soluble in typical solvents used in fabrication of semiconductor devices, such as y-butyrolactone, and may be employed in formulations that may be spin coated onto substrates and vitrified at a lower temperature and/or form a system which does not suffer a significant loss in modulus at elevated temperatures. Such compositions are desirable in order to obtain highly porous films having reduced potential for pore collapse or coalescence during the chip manufacturing process and that upon vitrification, result in a desirable low dielectric constant, insulating film.

DETAILED DESCRIPTION OF THE INVENTION

For purposes of United States patent practice, the contents of any patent, patent application or publication referenced herein is hereby incorporated by reference in its entirety herein, especially with respect to its disclosure of monomer, oligomer or polymer structures, synthetic techniques and general knowledge in the art. If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise, refers to the listed members individually as well as in any combination.

As used herein the term "aromatic" refers to a polyatomic, cyclic, ring system containing $(4\delta+2)$ electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings.

"A-functionality" refers to a single dienophile group.

"B-functionality" refers to the ring structure comprising two conjugated carbon-to-carbon double bonds and a leaving group L.

"B-Staged" refers to the oligomeric mixture or low molecular weight polymeric mixture resulting from partial polymerization of a monomer. Unreacted monomer may be included in the mixture.

"Cross-linkable" refers to a matrix precursor that is capable of being irreversibly cured, to a material that cannot be reshaped or reformed. Cross-linking may be assisted by UV, microwave, x-ray, or e-beam irradiation. Often used interchangeably with "thermosettable" when the cross-linking is done thermally.

"Dienophile" refers to a group that is able to react with the conjugated, double bonded carbon groups according to the present invention, preferably in a cycloaddition reaction involving elimination of the L group and aromatic ring formation.

"Inert substituent" means a substituent group which does not interfere with any subsequent desirable polymerization reaction of the monomer or B-staged oligomer and does not include further polymerizable ring structures as disclosed herein.

"Matrix precursor" means a monomer, prepolymer, or polymer, or mixtures thereof which upon curing forms a cross-linked matrix material.

"Monomer" refers to a polymerizable compound or mixture of polymerizable compounds.

"Matrix" refers to a continuous phase surrounding dispersed regions of a distinct composition or void.

"Poragen" refers to components which may be removed from the initially formed oligomer or polymer or, more preferably, from the vitrified (that is the fully cured or cross-linked) polymer, resulting in the formation of voids or pores in the polymer. Poragens may be removed from the matrix polymer by any suitable technique, including dissolving by solvents or, more preferably, by thermal decomposition.

"Unsymmetric" refers to the fact that only one of the conjugated, double bonded carbons of the B-functionality of the present monomer or only one carbon of a fused aromatic ring containing two of the conjugated, double bonded carbons is substituted with an aromatic ring to which the A-functional groups are attached.

The Monomers and Their Syntheses

The monomers of the present invention preferably comprise a single ring having two conjugated carbon to carbon double bonds and the leaving group, L and further substituted with the foregoing unsymmetric dienophilic functionality, or inertly substituted derivatives thereof. Examples of suitable ring structures include cyclopentadienones, pyrones, furans, thiophenes, pyridazines, and alkyl or aryl, including fused ring aryl, derivatives thereof.

Preferably, the ring structure is a five-membered ring where L is —O—, —S—, —(CO)—, or —(SO$_2$)—, or a six membered ring where L is —N=N—, or —O(CO)—. Optionally, two of the carbon atoms of the ring structure and their substituent groups taken together may form an aromatic ring, that is, the 5 or 6 membered ring structures may be fused to an aromatic ring.

Most preferably, L is —(CO)— such that the ring is a cyclopentadienone group or benzcyclopentadienone group. Examples of such most preferred cyclopentadienone rings are those containing aryl groups at the 2 and 5 positions thereof, more preferably at the 2, 4 and 5 positions thereof.

Preferred dienophile groups are hydrocarbon groups, most preferably ethynyl or phenylethynyl groups.

Examples of suitable monomers according to the invention are compounds corresponding to the formula, wherein L is —O—, —S—, —N=N—, —(CO)—, —(SO$_2$)—, or —O(CO)—;

Z is independently in each occurrence hydrogen, halogen, an unsubstituted or inertly substituted aromatic group, an unsubstituted or inertly substituted alkyl group, or two adjacent Z groups together with the carbons to which they are attached form a fused aromatic ring, and in one occurrence, Z is wherein, R$^1$ is independently each occurrence selected from the group consisting of hydrogen, halo, C$_{1-4}$ alkyl, C$_{6-60}$ aryl, and C$_{7-60}$ inertly substituted aryl groups; and R$^2$ is independently each occurrence selected from the group consisting of hydrogen, C$_{1-4}$ alkyl, C$_{6-60}$ aryl, and C$_{7-60}$ inertly substituted aryl groups.

Preferred monomers according to the present invention are 2- or 3-di(arylethynyl)aryl-substituted cyclopentadienone compounds, more preferably compounds represented by the formula:

wherein R$^3$ is C$_{6-20}$ aryl or inertly substituted aryl, most preferably, phenyl, biphenyl, p-phenoxyphenyl or naphthyl.

The monomers of the present invention or B-staged oligomers thereof are suitably employed in a curable composition alone or as a mixture with other monomers containing two or more functional groups (or B-staged oligomers thereof) able to polymerize by means of a Diels-Alder or similar cycloaddition reaction. Examples of such other monomers include compounds having two or more cyclopentadienone functional groups and/or acetylene functional groups or mixtures thereof, such as those previously disclosed in U.S. Pat. Nos. 5,965,679 and 6,359,091. In the B-stage curing reaction, a dienophilic group reacts with the cyclic diene functionality, causing elimination of L and aromatic ring formation. Subsequent curing or vitrification may involve a similar cycloaddition or an addition reaction involving only the dienophilic functional groups.

Additional suitable monomers that may be included in a curable composition according to the present invention include compounds of the formula:

(I)

wherein

Z' is independently in each occurrence hydrogen, an unsubstituted or inertly substituted aromatic group, an unsubstituted or inertly substituted alkyl group, or —W—(C≡C-Q)$_q$;

X' is an unsubstituted or inertly substituted aromatic group, —W—C≡C—W—, or

W is an unsubstituted or inertly substituted aromatic group, and

Q is hydrogen, an unsubstituted or inertly substituted C$_{6-20}$ aryl group, or an unsubstituted or inertly substituted C$_{1-20}$ alkyl group, provided that at least two of the X' and/or Z' groups comprise an acetylenic group, q is an integer from 1 to 3; and n is an integer of from 1 to 10.

Examples of the foregoing polyfunctional monomers that may be used in conjunction with the monomers of the present invention include compounds of formulas II-XXV:

Formula II:

Formula III (a mixture of):

and

Formula IV:

Formula V:

Formula VI:

Formula VII:

Formula VIII:

Formula IX:

Formula X:

Formula XI:

Formula XII:

Formula XIII:

Formula XIV:

Formula XV:

Formula XVI:

Formula XVII:

Formula XVIII

Formula XIX:

Formula XX (a mixture of):

-continued and

Formula XXI (a mixture of):

-continued and

Formula XXII (a mixture of):

and

Formula XXIII:

Formula XXIV:

Formula XXV:

The foregoing monomers II-XXV where the ring structure is a cyclopentadienone may be made, for example, by condensation of substituted or unsubstituted benzils with substituted or unsubstituted benzyl ketones (or analogous reactions) using conventional methods such as those disclosed in: Kumar, et al. Macromolecules, (1995), 28, 124-130, Ogliaruso et al., J. Org. Chem, (1965), 30, 3354, Ogliaruso, et al., J. Org. Chem., (1963), 28, 2725, Wiesler, et al., Macromolecules, (2001), 34, 187, Baker, et al., Macromolecules, (1979), 12, 369, Tong, et al., J. Am. Chem. Soc. (1997), 119, 7291, and U.S. Pat. No. 4,400,540. Monomers having other structures may be prepared as follows: Pyrones can be prepared using conventional methods such as those shown in the following references and references cited therein: Braham et. al., Macromolecules (1978), 11, 343; Liu et. al., J. Org. Chem. (1996), 61, 6693-99; van Kerckhoven et. al., Macromolecules (1972), 5, 541; Schilling et. al. Macromolecules (1969), 2, 85; Puetter et. al., J. Prakt. Chem. (1951), 149, 183. Furans can be prepared using conventional methods such as those shown in the following references and references cited therein: Feldman et. al., Tetrahedron Lett. (1992), 47, 7101, McDonald et. al. J. Chem. Soc. Perkin Trans. (1979), 1 1893. Pyrazines can be prepared using conventional methods such as those shown in the following reference and references cited therein: Turchi et. al., Tetrahedron (1998), 1809.

In a preferred embodiment of the invention employing mixtures of the present monomers and other monomers as previously disclosed it is desirable to maintain a ratio of the corresponding A-functionality and B-functionality in the mixture such that the ratio of B-functional groups to A-functional groups in the reaction mixture is in the range of 1:10 to 10:1, and most preferably from 2:1 to 1:4. Preferably, the composition additionally comprises a solvent and most preferably also comprises a poragen.

In a further preferred embodiment a composition comprising one or more monomers according to the present invention and optionally a poragen while curing forms a polyarylene material wherein the B-staged monomer composition has a flexural storage modulus profile as measured by torsional impregnated cloth analysis (TICA) characterized in that during heating of the composition a minimum measured modulus observed in the temperature range from 250 to 450° C., Mmnin, is of a greater magnitude than that shown by a conventional SiLK*-I™ material when analyzed in a similar manner, and preferably is at least 50 percent, more preferably at least 75 percent of the flexural storage modulus of the fully cured composite measured at 25° C. SiLK*-I™ is a commercially available polyarylene oligomer solution available from The Dow Chemical Company.

In the TICA method, a woven glass cloth (preferably, 0.3 mm thick, 15 mm wide, and 35 mm long) is mounted in a dynamic mechanical analyzer, such as a DuPont 983 DMA, preferably fitted with a Low Mass Vertical Clamp Accessory or equivalent functionality to enhance sensitivity. The ends of the cloth are wrapped in aluminum foil leaving 10 mm in length exposed. The cloth is then mounted in the vertical clamps of the dynamic mechanical analyzer which are set 10 mm apart. The clamps are tightened to 12 inch pounds (1.4 Nm) using a torque wrench. The cloth is impregnated using a solution comprising the B-staged monomers at 10 to 30 percent solids via a pipette. The cloth is thoroughly soaked with the solution and any excess is removed using the pipette. A heat deflector and oven are attached and a nitrogen flow of 3 standard cubic feet per hour (0.009 m$^3$/h) is established. Amplitude of the displacement is set to 1.00 mm and frequency is set to 1 Hz. The sample is heated to 500° C. at 5° C. per minute and then allowed to cool. Data is collected during both the heating and cooling stages. Data analysis may be performed to obtain temperature versus flexural storage modulus values for the composite of glass and formulation. Prepared software programs such as DMA Standard Data Analysis Version 4.2 from DuPont or Universal Analysis for Windows 95/98/NT Version 2.5H from TA Instruments, Inc., may be used to perform the data analysis. The flexural storage modulus values themselves are not absolute values for the tested formulation due to the contribution of the glass cloth and the unavoidable variation in sample loading. However, qualitative assessment of one matrix system versus another can be made if the differences are significant.

Although not wishing to be bound by theory, it is believed that upon heating a solvent containing mixture according to the invention, the initial solvent loss leads to an increase in the flexural storage modulus of the cloth/matrix composite. After further heating the flexural storage modulus begins to decrease as the temperature of the scan reaches and then exceeds the glass transition temperature of the mixture of the B-staged monomers. As the precursor compounds begin to react or cure the modulus again increases and then levels out as cure is complete. Upon cool-down the flexural storage modulus slowly increases in a fairly linear manner. If a significant drop in flexural storage modulus is observed between 300 and 400° C. during cure, pore collapse problems may result. The flexural storage modulus, Mmin, for the formulations of this invention may be greater than that which occurs in conventional formulations and/or Mmin may occur at a lower temperature, Tmin, e.g. less than 375° C. When employed in formulations including a poragen, this fact helps avoid pore collapse because it is less likely that significant degradation of the poragens will have occurred prior to reaching Tmin and/or the modulus will be sufficient to maintain the porosity.

Suitable solvents for use in preparing spin coating formulations of the monomers herein include known solvents useful in processing thermoset polyarylene precursor compositions. The solvent may be a single solvent or a mixture of one or more solvents. Examples include mesitylene, pyridine, triethylamine, N-methylpyrrolidinone (NMP), methyl benzoate, ethyl benzoate, butyl benzoate, cyclopentanone, cyclohexanone, cycloheptanone, cyclooctanone, cyclohexylpyrrolidinone, and ethers or hydroxy ethers such as dibenzylethers, diglyme, triglyme, diethylene glycol ethyl ether, diethylene glycol methyl ether, dipropylene glycol methyl ether, dipropylene glycol dimethyl ether, propylene glycol phenyl ether, propylene glycol methyl ether, tripropylene glycol methyl ether, toluene, xylene, benzene, dipropylene glycol monomethyl ether acetate, dichlorobenzene, propylene carbonate, naphthalene, diphenyl ether, butyrolactone, dimethylacetamide, dimethylformamide and mixtures thereof.

Suitable poragens for use herein include any compound that can form small domains in a matrix formed from the precursors and which can be subsequently removed, for example by thermal decomposition. Preferred poragens are polymers including homopolymers and interpolymers of two or more monomers including graft copolymers, emulsion polymers, and block copolymers. Suitable thermoplastic materials include polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of the monomers used to make these materials, and mixtures of these materials. The thermoplastic materials may be linear, branched, hyperbranched, dendritic, or star like in nature. The poragen may also be designed to react with the cross-linkable matrix precursor during or subsequent to B-staging to form blocks or pendant substitution of the polymer chain. For example, thermoplastic polymers containing reactive groups such as vinyl, acrylate, methacrylate, allyl, vinyl ether, maleimido, styryl, acetylene, nitrile, furan, cyclopentadienone, perfluoroethylene, BCB, pyrone, propiolate, or ortilo-diacetylene groups can form chemical bonds with the cross-linkable matrix precursor, and then the thermoplastic can be removed to leave pores. The poragen is desirably a material that results in formation of voids or pores in the matrix having an average pore diameter less than 200 nm, more preferably less than 100 nm, most preferably less than 50 nm. Suitable block copolymers include those wherein one of the blocks is compatible with cross-linked polymer matrix resin and the other block is incompatible therewith. Useful polymer blocks can include polystyrenes such as polystyrene and poly-α-methylstyrene, polyacrylonitriles, polyethylene oxides, polypropylene oxides, polyethylenes, polylactic acids, polysiloxanes, polycaprolactones, polyurethanes, polymethacrylates, polyacrylates, polybutadienes, polyisoprenes, polyvinyl chlorides, and polyacetals, and amine-capped alkylene oxides (commercially available as Jeffamine™ polyether amines from Huntsman Corp.).

Preferably, the martix precursor grafts to the porogen. This may be accomplished by adding the porogens to the monomers prior to B-staging as residual functional groups on the porogen are available to react with reactive groups on the monomers. Alternatively, some B-staging may occur prior to addition of the porogen and the porogen may be grafted by subjecting the mixture to conditions sufficient to cause residual functional groups on the porogen to react with residual reactive groups in the B-staged reaction product. The mixture is then coated onto a substrate (preferably solvent coated as for example by spin coating by known methods). The matrix is cured and the porogen is removed by heating it past its thermal decomposition temperature. Porous films prepared in this manner are useful in making integrated circuit articles where the film separates and electrically insulates conductive metal lines from each other.

Highly preferred poragens are crosslinked polymers made by solution or emulsion polymerization. Such polymerization techniques are known in the art, for example, EP-A-1, 245,586, and elsewhere. Very small crosslinked hydrocarbon based polymer particles have been prepared in an emulsion polymerization by use of one or more anionic-, cationic-, or non-ionic surfactants. Examples of such preparations may be found in *J. Dispersion Sci. and Tech.*, vol. 22, No. 2-3, 231-244 (2001), *The Applications of Synthetic Resin Emulsions*, H. Warson, Ernest Benn Ltd., 1972, p.88, and *Colloid Polyin. Sci.*, 269, 1171-1183 (1991), *Polymer. Bull*, 43, 417-424 (1999) and WO 2003 070777, among other sources.

The compositions of the invention may be used to make dielectric films and interlayer dielectrics for integrated circuits in accordance with known processes, such as those of U.S. Pat. No. 5,965,679. To make a porous film the poragen is preferably removed by thermal decomposition of the poragen.

The following examples are for illustrative purposes only and are not intended to limit the scope of this invention.

EXAMPLE 1

4-(3,5-bis(Phenylethynyl)phenyl)-2,3,5-triphenylcyclopentadienone

Synthesis of 1-Phenylethynyl-3,5-Dibromobenzil 1,3,5-Tribromobenzene (31.48 grams, 0.10 mole); phenylacetylene (10.22 grams, 0.10 mole); anhydrous, nitrogen sparged triethylamine (48.18 grams, 0.476 mole); triphenylphosphine (0.66 gram, 0.00253 mole); palladium (II) acetate (0.09 gram, 0.00041 mole) and anhydrous, nitrogen sparged N,N-dimethylformamide (90 milliliters) were added under a dry nitrogen atmosphere to a predried 500 milliliter glass three neck round bottom reactor containing a predried magnetic stirring bar. The reactor was additionally outfitted with a fan cooled spiral condenser and a thermometer with thermostatically controlled heating mantle. Stirring and heating commenced, and after 14 minutes, when a temperature of 35° C. was achieved, a clear, light amber colored solution formed. After a cumulative 1.6 hours reaction time, a temperature of 80° C. was achieved and maintained for the next 17.2 hours. At this time, high pressure liquid chromatographic (HPLC) analysis indicated that full conversion of the phenylacetylene reactant had been achieved. The reactor contents were poured over cracked ice contained in a 2 liter beaker. After complete melting of the ice, the precipitated product was recovered via filtration through a medium fitted glass funnel. The product cake on the funnel was washed with two portions (100 milliliter) of deionized water, then directly recrystallized, as a damp product, from boiling ethanol (350 milliliters total volume at boiling). The recrystallization solution was allowed to cool to room temperature and held there for 16 hours to provide 17.1 grams of a light yellow fibrous crystalline product after recovery via filtration and drying under vacuum (40° C. and 1 mm Hg). HPLC analysis revealed the presence of the desired 1-phenylethynyl-3,5-dibromobenzene product at 89 area percent, residual 1,3,5-tribromobenzene at 4 area percent and the 7 area percent balance as a single unknown. The spectrum as determined by $^1$H nuclear magnetic resonance (NMR) analysis was consistent with the desired product.

Synthesis of 3,5-Dibromobenzil

A portion of the product containing 1-phenylethynyl-3,5-dibromobenzene (6.94 grams) and dimethylsulfoxide (100 milliliters) were added to a 500 milliliter glass three neck round bottom reactor outfitted with a chilled (2° C.) condenser, a thermometer with thermostatically controlled heating mantle, and a magnetic stirring bar. The reactor contents were heated as a stirred solution to 140° C., then iodine (0.07 gram, 0.00055 mole) was added. After 3 days at the 140° C. reaction temperature, the hot product solution was cooled to 25° C., resulting in the formation of a yellow crystalline slurry. The slurry was added to a beaker containing a stirred mixture of 10 percent aqueous sodium hydrosulfite (87 milliliters), deionized water (100 milliliters) and diethyl ether (200 milliliters). After stirring for one hour, the diethyl ether layer was recovered in a separatory funnel, then washed with three portions (75 milliliter) of deionized water. The recovered diethyl ether solution was dried over anhydrous sodium sulfate and filtered through a medium fitted glass funnel to provide a filtrate which was then rotary evaporated to dryness. The crude product was recrystallized from boiling ethanol. The recrystallization solution was allowed to cool to room temperature and held therein for 16 hours to provide 5.70 grams of a light yellow fluffy crystalline product. HPLC analysis revealed the presence of the desired 3,5-dibromobenzil product at 99 area percent with the 1 area percent balance as a single unknown. The $^1$H NMR spectrum corresponded to that of the desired product.

Synthesis of 3,5-bis(Phenylethynyl)benzil 3,5-Dibromobenzil (12.50 grams, 0.0679 bromine equivalent); phenylacetylene (8.40 grams, 0.0822 mole); anhydrous, nitrogen sparged triethylamine (18.77 grams, 0.186 mole); triphenylphosphine (0.45 gram, 0.0017 mole); palladium (II) acetate (0.06 gram, 0.00028 mole) and anhydrous, nitrogen sparged N,N-dimethylformamide (79 milliliters) were added under a dry nitrogen atmosphere to a predried 500 milliliter glass three neck round bottom reactor containing a predried magnetic stirring bar. The reactor was additionally outfitted with a fan cooled spiral condenser and a thermometer with a thermostatically controlled heating mantle. Stirring and heating of the light amber colored solution was commenced and after 13 minutes, a temperature of 80° C. was achieved and maintained for the next 15.1 hours. At this time, HPLC analysis indicated that full conversion of the 3,5-dibromobenzil reactant had been achieved. The reactor contents were poured over cracked ice contained in a 2 liter beaker. After complete melting of the ice, the precipitated product was recovered via filtration through a medium fitted glass funnel. The product cake on the funnel was washed with two portions (100 milliliter) of deionized water, then directly recrystallized, as a damp product, from boiling acetone (160 milliliters total volume at boiling). The recrystallization solution was allowed to cool to room temperature and held therein for 16 hours to provide 10.90 grams (78.2 percent isolated yield) of a yellow fibrous crystalline product after recovery via filtration and drying under vacuum (40° C. and 1 mm Hg). HPLC analysis revealed the presence of the desired 3,5-bisphenylethynyl)benzil product at 100 area percent. The $^1$H NMR spectrum was consistent with the desired product. The product identity was confirmed by electron ionization mass spectroscopic analysis (EI MS).

Synthesis of 4-(3,5-bis(Plenyletliynyl)phenyl)-2,3,5-triphetlylcyclopelztadieone A portion of the 3,5-bis(phenylethynyl)benzil (10.87 grams, 0.0265 mole), 1,3-diphenylacetone (5.90 grams, 0.0281 mole), anhydrous 1-propanol (300 milliliters) and anhydrous toluene (17 milliliters), both of which had been sparged with dry nitrogen, were added under a dry nitrogen atmosphere to a predried 500 milliliter glass three neck round bottom reactor containing a predried magnetic stirring bar. The reactor was additionally outfitted with a fan cooled spiral condenser and a thermometer with thermostatically controlled heating mantle. Stirring and heating commenced, and once a refluxing clear light yellow colored solution formed, benzyltrimethylammonium hydroxide (40 percent in methanol) (0.91 gram) was added, immediately inducing a dark red color. After maintaining the reflux for 20 reactant had been achieved. After a cumulative 30 minutes of reaction, the heating mantle was removed from the reactor, and the stirred contents were maintained at 24° C. for the next 16 hours. The product was recovered via filtration through a medium fitted glass funnel. The product cake on the funnel was washed with two portions (50 milliliters) of 1-propanol, then dried in a vacuum oven to provide 11.84 grams (76.4 percent isolated yield) of 4-(3,5-bis(phenylethynyl)phenyl)-2,3,5-triphenylcyclopentadienone (unsymmetrically substituted 3,5-AAB monomer) as a dark red purple colored crystalline product. HPLC analysis revealed the presence of the desired product at 100 area percent. The product's identity was confirmed by $^1$H NMR and El MS analysis.

EXAMPLE 2

Alternate Synthesis of 4-(3,5-bis(phenylethynyl) phenyl)-2,3,5-triphenylcyclopentadienone 3,5-bis(phenylethynyl)benzil (65.6 grams, 0.16 mole) prepared in the manner of Example 1,1,3-diphenylacetone (37.8 grams, 0.18 mole), 2-propanol (583 milliliters) and toluene (218 milliliters), were added to a 2 liter glass four neck Morton reactor containing a magnetic stirring bar. The reactor was additionally outfitted with chilled (2° C.) condenser, a thermometer with thermostatically controlled heating mantle and a subsurface tube for sparging with nitrogen. Under a nitrogen atmosphere, an addition funnel was loaded with tetrabutylammonium hydroxide (1M in methanol) (5.46 milliliters) diluted into 2-propanol (97 milliliters) which had been sparged with nitrogen. This addition funnel was then attached to the reactor under dynamic nitrogen flow. Sparging and heating of the stirred slurry commenced, and after 42 minutes, once a reflux (80° C.) was achieved, a clear light yellow colored solution had formed. At this time, the sparge tube was move up out of the solution in the reactor to provide nitrogen overhead, then dropwise solution of the catalyst commenced, inducing the formation of a dark red color. After 92 minutes at reflux, 44 milliliters of the catalyst solution had been added and HPLC analysis indicated that full conversion of the 3,5-bis[phenylethynyl] benzil reactant had been achieved, with minimum formation of coproducts. After a cumulative 101 minutes at reflux, the heating mantle was removed from the reactor, additional 2-propanol was added (413 milliliters), then an ice bath was placed under the reactor and the stirred contents were maintained therein for the next 39 minutes until a temperature of 5° C. was achieved. The product was recovered via filtration through a coarse flitted glass funnel. The product cake on the funnel was washed with two portions (50 milliliters) of 2-propanol, giving a clear filtrate with the second wash. Drying in a vacuum oven to provided 79.66 grams (85.3 percent isolated yield) of 4-(3,5-bis(phenylethynyl)-phenyl)-2,3,5-triphenylcyclopentadienone (unsymmetrically substituted 3,5-AAB monomer) as a dark red purple colored crystalline product. HPLC analysis revealed the presence of the desired product at 100 area percent.

Physical Property Testing

Solubility in γ-Butyrolactone

Three 0.100 g portions of 4-(3,5-bisphenylethynyl)phenyl)-2,3,5-triphenylcyclopentadienone from three separate syntheses were weighed into glass vials along with 0.750 gram of γ-butyrolactone. Each vial was sealed and then allowed to stand for 24 hours at 23.5° C. with gentle agitation. The contents of each respective vial was then loaded into a disposable plastic syringe and filtered through a 0.2 μm PTFE syringe filter. The liquid from each of the filters was weighed into disposable aluminum pans then devolatilized to a constant weight in a vacuum oven maintained at 60° C. The results thus obtained allowed calculation of a solubility for the three samples of 5.09, 5.16 and 5.26 percent in γ-butyrolactone at 23.5° C.

Comparison experiments employing 3,4-bis-(3-(phenylethynyl)phenyl)-2,5-diphenylcyclopentadienone (3,3'-AAB monomer) and 3,4-bis-(4-(phenylethynyl)phenyl)-2,5-diphenylcyclopentadienone (4,4'-AAB monomer) gave <0.10 and 0.30 weight percent respectively.

Analysis by Differenitial Scaning Calorimeter (DSC)

DSC was completed using 3.5 and 3.0 milligram samples for duplicate analysis of 4-(3,5-bis(phenylethynyl)phenyl)-2,3,5-triphenylcyclopentadienone. A DSC 2920 Modulated DSC (TA Instruments) was employed, using a heating rate of 7° C. per minute from 25° C. to 500° C. under a stream of nitrogen flowing at 45 cubic centimeters per minute. The results represent the average from the pair of analyses. A single sharp endothermic melting point transition was observed with a minimum at 187.8° C. (87.5 joules per gram). A single exothermic transition, attributable to Diels Alder reaction of phenylethynyl groups with cyclopentadienone groups, was observed with a maximum at 229.0° C. (169.9 joules per gram). The onset temperature for this exothermic transition was 196.4° C., while the ending temperature was 290.8° C. A second exothermic transition, attributable to reaction of phenylethynyl groups, was observed with a maximum at 410.6° C. (47.5 joules per gram). The onset temperature for this exothermic transition was 363. 1° C., while the ending temperature was 465.2° C. The samples recovered from the DSC analysis were rigid light yellow colored fused transparent solids.

EXAMPLE 3

B-Staging of Monomer

In a dry nitrogen glove box, a portion (6.05 grams) of 4-(3,5-bis(phenylethynyl)phenyl)-2,3,5-triphenylcyclopentadienone and γ-butyrolactone (14.12 grams), which had been sparged with dry nitrogen, were added to a 100 milliliter glass three neck round bottom reactor containing a 17 mm starhead TFE magnetic stirrer. The reactor was additionally outfitted with a fan cooled spiral condenser and a thermometer with thermostatically controlled heating mantle. The heating mantle surface additionally possessed a thermocouple for direct reading of the surface temperature. Stirring commenced, and a sample of the homogeneous slurry was taken for gel permeation chromatography (GPC). All GPC analysis was completed using tetrahydrofuran as the eluent and polystyrene calibration standards. Heating commenced, and after 35 minutes, a temperature of 195° C. was achieved and maintained. The heating mantle surface temperature required to maintain the 195° C. internal temperature for the B-stage reaction ranged between 220°C and 235° C. After 7, 12, 24 and 48 hours of B-stage reaction, samples of the solution were taken and analyzed by GPC. Results are contained in Table 1

TABLE 1

| Sample (hours) | Mn | Mw | Polydispersity Index |
|---|---|---|---|
| Initial (0) | 510 | 460 | 0.90 |
| 7 | 2,120 | 2,740 | 1.29 |
| 12 | 2,650 | 3,620 | 1.37 |

TABLE 1-continued

| Sample (hours) | Mn | Mw | Polydispersity Index |
|---|---|---|---|
| 24 | 3,600 | 5,680 | 1.58 |
| 48 | 5,330 | 9,580 | 1.80 |

At the 48 hour B-stage reaction time, the product was an easily stirred dark red amber colored solution. All samples were free of any visually observable gels.

EXAMPLE 4

Composite Preparation and Testing

Figure 1:
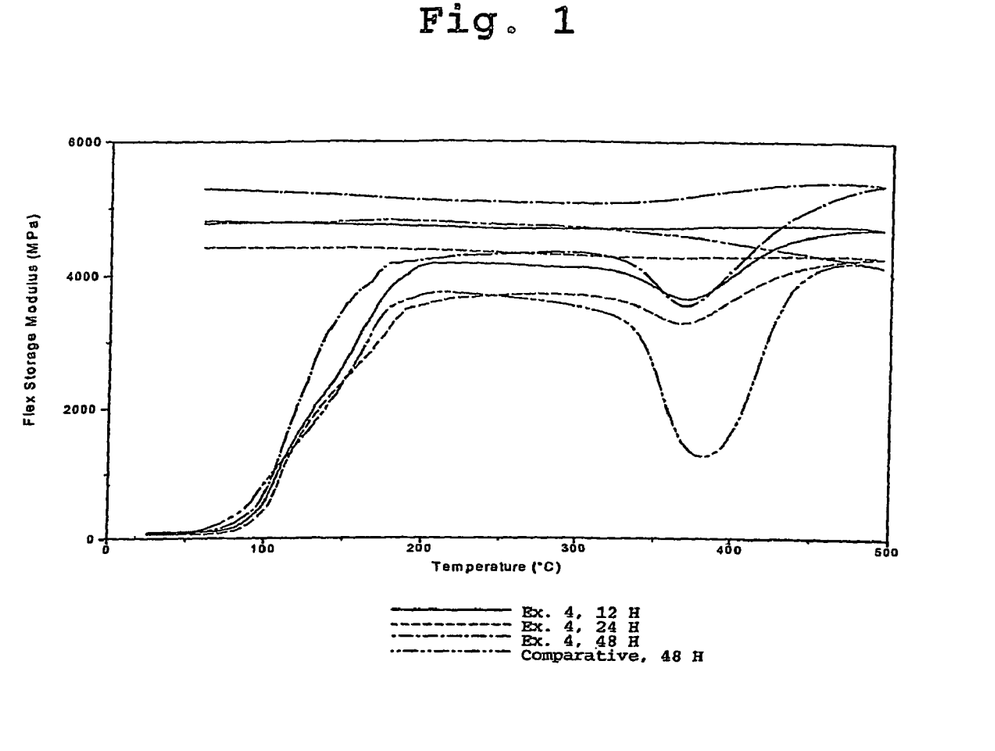
FIG. 1 contains TICA plots of a polymer formulation according to the invention and of a comparison conventional formulation.

Three solutions of B-staged 4-(3,5-bis(phenylethynyl) phenyl)-2,3,5-triphenylcyclopentadienone representing three different B-stage times (12, 24, and 48 hours) as approximately 20 percent solids solutions in γ-butyrolactone/cyclohexanone (50/50 by volume) were evaluated by torsional impregnated cloth analysis (TICA). The solutions were applied to a cloth braid fixed in a DuPont 983 DMA then ramped at 5° C./minute from room temperature to 500° C. followed by an uncontrolled cooling to 60° C. The flexural storage modulus was determined as a function of temperature and compared to similar data obtained for a conventional spin coated dielectric resin formulation (SiLK*-I™ resin available from The Dow Chemical Company, 48 hours B-staging time). The results are shown in FIG. 1.

The plots show an increase in modulus as the temperature increases as a result of solvent loss from the B-staged resin. After the solvent is removed the modulus is fairly flat until the glass transition temperature of the oligomers is exceeded and the modulus begins to drop. As the temperature increases to the point where phenylethynyl-phenylethynyl cure chemistry begins to occur (>320° C.) the modulus reaches a minimum and begins to increase as the crosslinked network forms. When the phenylethynyl-phenylethynyl cure is essentially complete the modulus value levels off and then upon cooling the modulus is fairly flat indicating that no gross decomposition has occurred.

The plots for the two resins are similar with the exception of the magnitude of the modulus drop in the 320-420° C. temperature range for the invented resin is significantly less than that of the comparative system, regardless of the B-staging time. It is desirable to provide a resin having minimal modulus loss in this temperature regime to avoid collapse of pores during decomposition of a poragen. If the poragen were to decompose at a point where the modulus of the matrix is low, pore collapse may result.

EXAMPLE 5

Poragen Containing Composition

A 2.00 gram sample of 4-3,5-bis(phenylethynyl)phenyl)-2,3,5-triphenylcyclopenta-dieneone was placed in a 50 mL round bottom, long neck flask equipped with a side arm stop cock valve connected to a vacuum line, a magnetic stirring bar, and a serum cap at the top. In addition, 0.67 grams of crosslinked styrene/divinylbenzene copolymer particles having volume average particle diameter (Dv) of 21 nm, made according to the procedure of WO 2003 070777, published Aug. 28, 2003, were added to the flask, along with 5.0 mL of electronic grade γ-butyrolactone solvent. The mixture was allowed to stir at ambient temperature for two hours and then it was degassed by repeated evacuation and flushing with dry, oxygen-free nitrogen. The flask was then placed in an oil bath at 150° C. with the stop cock valve open to a positive pressure of nitrogen gas. Once stirring was commenced, the reaction mixture was heated to 200° C. The B-staging reaction was allowed to proceed for 48 hours with small samples being taken at 24 and 48 hours. GPC analyses of these samples yielded the relative molecular weight data contained in Table 2

TABLE 2

| Reaction Time | Mn | Mw | Mp | Polydispersity |
|---|---|---|---|---|
| 24 hours | 2641 | 4204 | 3542 | 1.59 |
| 48 hours | 3844 | 7168 | 6319 | 1.86 |

The B-staged solution was cooled to approximately 150° C. and 7.85 mL of electronic grade cyclohexanone was introduced to provide a spin coating composition having an approximate solids concentration of 17 percent.

EXAMPLE 6

Preparation and Testing of Porous Thin Films

The poragen containing solution was filtered through a 1.0 μm pore sized cartridge filter and spun onto a silicon wafer. The coated wafer was then placed on a hot plate at 150° C. for 2 minutes under a nitrogen atmosphere to bake off the solvents. After cooling, the coated wafer was placed in a programmable furnace with a nitrogen atmosphere and the temperature was raised to 430° C. at 7° C./min and then held at 430° C. for at least 40 minutes. Upon cooling, the wafer was evaluated by measuring the light scattering index, the refractive index, and the change in film thickness. The results were: refractive index=1.4842, light scattering index=11.5, and percent thickness loss=7.1

Figure 2:
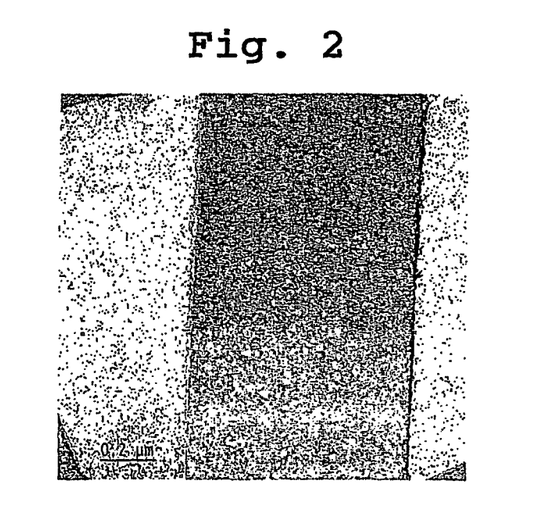
FIG. 2 is a transmission electron micrograph of a film prepared according to Example 6.

The film was also analyzed by transmission electron microscopy (TEM) and shown to provide a porous, durable, dielectric film A representative micrograph is shown in FIG. 2.

EXAMPLE 7

Spin Coating Composition with Varying Sized Poragen Material

Spin coating compositions of 4-(3,5-bis(Phenylethynyl) phenyl)-2,3,5-triphenylcyclopentadienone with crosslinked styrene/divinylbenzene microemulsion polymerized particles of varying particle size at 20 percent loading level and γ-butyrolactone diluent were B-staged by heating to 200° C. for 48 hours. A comparative coating composition comprising a symmetrically substituted 3,3'-AAB monomer, 3,4-bis(3-(phenylethynyl)phenyl)-2,5-diphenylcyclopentadienone, was similarly prepared.

The pore forming materials were prepared by the technique of microemulsion polymerization using a free radical initiator comprising only nitrogen, carbon and oxygen and a non-ionic surfactant as disclosed in WO 2003 070777. An especially desirable emulsion polymerization is conducted at 30° C., using high purity deionized water; a nonylphenol ethoxylate surfactant such as Tergitol™ NP-15, available from The Dow Chemical Company; a 90/10 (w/w) styrene/divinylbenzene monomer mix; and a free radical initiator comprising t-butylhydroperoxide and ascorbic acid to give very small, <50 nm Dv, poragen particles.

The resultant solutions were diluted with cyclohexanone to give 20 percent solids solutions. These solutions were then spun coat onto silicon wafers, cured, and the poragen removed by thermal degradation. The resultant porous films were then evaluated by Fourier Transform Infrared Spectroscopy (FT-IR) to assess density, by profilometry to determine thickness loss during cure, by Metricon analysis to determine refractive index, by light scattering to determine a light scattering index (LSI), by transmission electron microscopy (TEM) to determine average pore size and pore size range, by small angle x-ray scattering (SAXS) to determine pore size. In addition, the dielectric constants of the resulting cured porous films were measured. Results are contained in Table 3.

TABLE 3

|  | Invention | | Comparative | |
| --- | --- | --- | --- | --- |
| Poragen average particle diameter (nm) | 38 | 19 | 38 | 19 |
| Percent Density Retained (ether band at 1240 cm$^{-1}$) | 80 | — | 80 | — |
| Percent Thickness Loss | 0.53 | 3.00 | 4.11 | 4.48 |
| Refractive Index | 1.5006 | 1.5248 | 1.5097 | 1.5238 |
| Light Scattering Index | 39.20 | 10.45 | 54.40 | 14.75 |
| Pore Size Range (nm) | 9-52.5 | 8.5-32 | 12-54 | 7-33 |
| Mean Pore Size (nm) | 33.5 | 20.0 | 34.0 | 20.0 |
| SAX mean | — | 12.00 | — | 12.1 |
| Dielectric Constant | 2.29 | 2.4 | 2.28 | 2.39 |

What is claimed is:

1. A monomer corresponding to the formula:

wherein L is —O—, —S—, —N=N—, —(CO)—, —(SO$_2$)—, or —O(CO)—;

Z is independently in each occurrence hydrogen, halogen, an unsubstituted or inertly substituted aromatic group, an unsubstituted or inertly substituted alkyl group, or two adjacent Z groups together with the carbons to which they are attached form a fused aromatic ring, and in one occurrence, Z is wherein,

R$^1$ is independently each occurrence selected from the group consisting of hydrogen, halo, C$_{1-4}$ alkyl, C$_{6-60}$ aryl, and C$_{7-60}$ inertly substituted aryl groups; and R$^2$ is independently each occurrence selected from the group consisting of hydrogen, C$_{1-4}$ alkyl, C$_{6-60}$ aryl, and C$_{7-60}$ inertly substituted aryl groups.

2. A monomer according to claim 1 which is a 2- or 3-di(arylethynyl)aryl-substituted cyclopentadienone compound.

3. A monomer according to claim 2 represented by the formula:

wherein R3 is C$_{6-20}$ aryl or inertly substituted aryl.

4. A monomer according to claim 3 where in R3 is phenyl, biphenyl, p-phenoxyphenyl or naphthyl.

5. A monomer comprising a single aromatic ring that has two acetylenic groups attached to it, and said single aromatic ring being directly, covalently attached to a 2,4-cyclopentadienone or benz-2,4-cyclopentadienone ring structure, characterized in that the cyclopentadienone of one monomer is capable of reacting under cycloaddition reaction conditions with an acetylene group of a second monomer, thereby resulting in formation of an aromatic ring.

6. A spin-coatable, curable composition comprising a monomer according to claim 1, an optional solvent, and an optional pore forming material.

7. A spin-coatable, curable composition comprising a monomer according to claim 5, an optional solvent, and an optional pore forming material.

8. A method of forming an insulating film on an electrical device comprising coating the device with a composition according to claim 6, removing the optional solvent, curing the monomer, and optionally removing the optional pore forming material.

9. A method of forming an insulating film on an electrical device comprising coating the device with a composition according to claim 7, removing the optional solvent, curing the monomer, and optionally removing the optional pore forming material.

10. An electrical device comprising an insulating film prepared according to claim 8.

11. An electrical device comprising an insulating film prepared according to claim 9.

* * * * *